United States Patent
Jan et al.

(10) Patent No.: US 11,208,365 B2
(45) Date of Patent: Dec. 28, 2021

(54) PROCESSES AND APPARATUSES FOR METHYLATION OF AROMATICS IN AN AROMATICS COMPLEX

(71) Applicant: UOP LLC, Des Plaines, IL (US)

(72) Inventors: Deng-Yang Jan, Elk Grove Village, IL (US); Timur V. Voskoboynikov, Arlington Heights, IL (US); Mark B. Koch, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/809,868

(22) Filed: Nov. 10, 2017

(65) Prior Publication Data

US 2018/0170831 A1 Jun. 21, 2018

Related U.S. Application Data

(60) Provisional application No. 62/436,884, filed on Dec. 20, 2016.

(51) Int. Cl.
*C07C 2/86* (2006.01)
*B01J 29/70* (2006.01)

(52) U.S. Cl.
CPC .............. *C07C 2/864* (2013.01); *B01J 29/70* (2013.01); *B01J 29/7038* (2013.01);
(Continued)

(58) Field of Classification Search
CPC ......... C07C 2/862; C07C 2/864; C07C 2/865; C07C 2/867; C07C 2521/04;
(Continued)

(56) References Cited

U.S. PATENT DOCUMENTS 4,761,513 A 8/1988 Steacy et al.
4,929,358 A 5/1990 Koenitzer
(Continued)

FOREIGN PATENT DOCUMENTS

CN 1721378 A 1/2006
CN 1245477 C 3/2006
(Continued)

OTHER PUBLICATIONS

Adebajo et al., The contribution of the methanol-to-aromatics reaction to benzene methylation over ZSM-5 catalysts, Catalysis Communications,v 4, n 2, p. 71-76, Feb. 2003.
(Continued)

*Primary Examiner* — Youngsul Jeong
*Assistant Examiner* — Jason Y Chong

(57) ABSTRACT

Processes and apparatuses for benzene and/or toluene methylation under conditions of low temperatures in one of a vapor phase, a liquid phase or a mixed vapor-liquid phase, in an aromatics complex for producing para-xylene are described. More specifically, a process for producing a xylene isomer comprising reacting oxygenates with an aromatic feedstock comprising toluene and/or benzene in a methylation zone operating under alkylation conditions including one of a vapor, a liquid phase or a mixed vapor-liquid phase in the presence of a catalyst to provide a product stream comprising the xylene isomer is described.

20 Claims, 3 Drawing Sheets

(52) U.S. Cl.
CPC ...... *C07C 2521/04* (2013.01); *C07C 2521/08* (2013.01); *C07C 2529/70* (2013.01); *Y02P 20/50* (2015.11); *Y02P 20/52* (2015.11)

(58) Field of Classification Search
CPC .. C07C 2521/08; C07C 2529/70; B01J 29/70; B01J 29/7038; Y02P 20/52; Y02P 20/588
USPC .................................................... 585/467
See application file for complete search history.

(56) References Cited

U.S. PATENT DOCUMENTS

| | | | |
|---|---|---|---|
| 5,171,915 A | 12/1992 | Forbus et al. | |
| 5,349,114 A | 9/1994 | Lago et al. | |
| 5,477,184 A | 12/1995 | Uda et al. | |
| 5,939,597 A | 8/1999 | Dessau et al. | |
| 5,939,797 A | 8/1999 | Takesi et al. | |
| 6,642,426 B1 | 11/2003 | Johnson et al. | |
| 6,740,788 B1 | 5/2004 | Maher et al. | |
| 6,756,030 B1* | 6/2004 | Rohde | B01J 29/70 208/46 |
| 7,060,864 B2 | 6/2006 | Ghosh et al. | |
| 7,268,267 B2 | 9/2007 | Jan et al. | |
| 7,446,069 B2 | 11/2008 | Ghosh et al. | |
| 7,638,667 B2 | 12/2009 | Jan et al. | |
| 7,663,010 B2 | 2/2010 | Levin | |
| 7,812,208 B2 | 10/2010 | Cheng et al. | |
| 7,982,084 B1* | 7/2011 | Moscoso | C07C 2/12 208/111.01 |
| 7,985,886 B1* | 7/2011 | Jan | C07C 2/66 585/467 |
| 8,399,727 B2 | 3/2013 | Lattner et al. | |
| 8,450,232 B2 | 5/2013 | Yeh et al. | |
| 9,302,953 B2 | 4/2016 | Molinier et al. | |
| 9,446,961 B2 | 9/2016 | Johnson et al. | |
| 2004/0015027 A1* | 1/2004 | Iaccino | C10G 63/02 585/448 |
| 2004/0097769 A1* | 5/2004 | Ou | C07C 2/862 585/454 |
| 2004/0199036 A1* | 10/2004 | Jan | B01J 29/06 585/467 |
| 2005/0027151 A1 | 2/2005 | Ghosh et al. | |
| 2005/0143613 A1* | 6/2005 | Dakka | B01J 29/40 585/467 |
| 2009/0187056 A1* | 7/2009 | Chewter | C07C 1/20 585/638 |
| 2009/0253949 A1* | 10/2009 | Ghosh | B01J 29/06 585/454 |
| 2011/0243838 A1* | 10/2011 | Moscoso | C01B 39/48 423/709 |
| 2013/0137910 A1* | 5/2013 | Vincent | C07C 2/66 585/447 |
| 2013/0324779 A1 | 12/2013 | Heeter et al. | |
| 2014/0206909 A1* | 7/2014 | Calaresu | C07C 2/864 568/798 |
| 2014/0213840 A1 | 7/2014 | Helton et al. | |
| 2014/0296598 A1 | 10/2014 | Heeter et al. | |
| 2014/0336436 A1 | 11/2014 | Bender et al. | |
| 2015/0073187 A1 | 3/2015 | Ghosh et al. | |
| 2015/0376086 A1 | 12/2015 | Tinger et al. | |
| 2016/0024393 A1* | 1/2016 | Beech, Jr. | B01J 23/70 585/321 |
| 2016/0046544 A1 | 2/2016 | Molinier et al. | |
| 2016/0060542 A1* | 3/2016 | Sugita | C10G 3/42 585/408 |
| 2017/0368540 A1 | 12/2017 | Mettler et al. | |
| 2018/0099913 A1* | 4/2018 | Chen | B01J 29/70 |
| 2018/0099915 A1 | 4/2018 | Chen | |
| 2018/0251413 A1* | 9/2018 | Loveless | C07C 6/10 |
| 2019/0359542 A1 | 11/2019 | Detjen et al. | |

FOREIGN PATENT DOCUMENTS

| | | |
|---|---|---|
| CN | 1775175 A | 5/2006 |
| CN | 103121912 A | 5/2013 |
| CN | 103263946 A | 8/2013 |
| CN | 103588612 A | 2/2014 |
| CN | 105439790 A | 3/2016 |
| CN | 105503508 A | 4/2016 |
| CN | 105503509 A | 4/2016 |
| CN | 105646132 A | 6/2016 |
| EP | 249913 A1 | 12/1987 |
| GB | 1474065 A | 5/1977 |
| JP | 58199044 A | 11/1983 |
| JP | 62063528 A | 3/1987 |
| JP | H10502908 H | 3/1998 |
| JP | 2007533586 A | 11/2007 |
| JP | 2008544986 A | 12/2008 |
| JP | 2013523583 A | 6/2013 |
| JP | 2014531390 A | 11/2014 |
| KR | 1020060109503 | 10/2006 |
| RU | 2083730 C1 | 7/1997 |
| WO | 95013998 A1 | 5/1995 |
| WO | 2000040527 | 7/2000 |
| WO | 2004074219 A2 | 9/2004 |
| WO | 2005068406 A1 | 7/2005 |
| WO | 2011123337 A2 | 10/2011 |
| WO | 2016081110 A1 | 5/2016 |
| WO | 2017105848 A1 | 6/2017 |
| WO | 2017172067 A1 | 10/2017 |
| WO | 2018067281 A1 | 4/2018 |

OTHER PUBLICATIONS

Adebajo et al., Methylation of benzene with methanol over zeolite catalysts in a low pressure flow reactor, Catalysis Today, v 63, n 2-4, p. 471-478, Dec. 25, 2000.

Ahn et al., Methanol usage in toluene methylation with medium and large pore zeolites, ACS Catalysis, v 3, n 5, p. 817-825, May 3, 2013.

Chen et al., Continuous liquid phase acylation of toluene over HBEA zeolite: Solvent effects and origin of the deactivation. Journal of Molecular Catalysis A: Chemical, v 396, p. 231-238, Jan. 1, 2015.

Tangestanifard et al., Methylation of toluene with methanol in sub/supercritical toluene using H-beta zeolite as catalyst. Journal of Supercritical Fluids, v 113, p. 80-88, Jul. 2016.

Hu et al., The effect of Si/Al ratio on the catalytic performance of hierarchical porous ZSM-5 for catalyzing benzene alkylation with methanol, Catalysis Science and Technology, v 6, n 8, p. 2647-2652, Apr. 21, 2016.

PCT Search Report dated Mar. 15, 2018 for corresponding PCT Application No. PCT/US2017/065535.

Bajus, et al., Steam Cracking of Hydrocarbons-4. An Analysis of the High-Boiling (Polynuclear Aromatic Hydrocarbon) Products from (Steam Cracking of) Naphtha in a Quartz (Tubular) Reactor, Ind. Eng. Chem., Prod. Res. Dev. V19, N.4, 564-68 (Dec. 1980).

Ducarme, et al., ZSM-5 and ZSM-11 Zeolites: Influence of Morphological and Chemical Parameters on Catalytic Selectivity and Deactivation, Applied Catalysis, 17 (1985), 175-184.

Das, et al., Aromatization of C4-C6 hydrocarbons to benzene, toluene and para xylene over pore sized controlled ZnO-HZSM-5 zeolite, Catalysis Society of India 13th National Symposium and Silver Jubilee Symposium (Dehradun Apr. 2-4, 1997), Studies in Surface Science and Catalysis V113 447-53, 1998.

International Search Report and Written Opinion from corresponding PCT Application No. PCT/US2018/064022, dated Mar. 21, 2019.

International Search Report and Written Opinion from corresponding PCT Application No. PCT/US2019/023673, dated Jun. 20, 2019.

Wu, et al., Selective formation of p-xylene with disproportionation of toluene over MCM-22 catalysts, Microporous and Mesoporous Materials (ISSN 1387-1811), V. 22., n. 1-3, 343-56, Jun. 17, 1998.

(56) References Cited

OTHER PUBLICATIONS

Chareonpanich, et al., Remarkable increase of BTX yield by zeolite catalyst in the hydrocracking of coal volatile matter, Coal. Sci. Technol., 24 (Coal Sciene, vol. 2) 1483-6 (1995) Chemical Abstracts (ISSN 0009-2258) Abstr. No. 150548 V124 N.12, 1995, p. 1483-1486.
Chareonpanich, et al., The hydrocracking of aromatic hydrocarbons over USY-zeolite, Energy & Fuels (ISSN 0887-0624) V10 N.4, 927-31 (Jul. 1996.).
Schwanke, Anderson, et al., Lamellar MWW-Type Zeolites: Toward Elegant Nanoporous Materials, Applied Sciences, 2018, 8, 1636, doi: 10.3390.
International Preliminary Report for PCT application No. PCT/US2017/065535, dated Jun. 25, 2019.
International Preliminary Report for PCT application No. PCT/US2018/064022, dated Jun. 9, 2019.
International Preliminary Report for PCT application No. PCT/US2019/023673, dated Sep. 29, 2020.
Zhao, Wenping, Aromatization and Alkylation of Methanol on Nano HZSM-5 and HMCM-22 Zeolites, Chinese Doctoral Dissertations Full-text Database Engineering Science and Technology I, B014-27, published on Jul. 15, 2015 (Relevant part only).
Fu, Liping, et al., Studies on Alkylation of Toluene over MgO Modified MCM-22 Prepared by Complexation Impregnation, Specialty Petrochemicals, vol. 29, No. 2, pp. 48-53, published Mar. 31, 2012 (Abstract only).
Yongxin, Li et al., Synthesis of HMCM-22/MCM-41 and Catalytic performance for toluene alkylation with dimethyl carbonate. Chemical Industry and Engineering Progress, vol. 29, No. 5, pp. 875-879, published Dec. 31, 2010 (abstract only).

* cited by examiner

PROCESSES AND APPARATUSES FOR METHYLATION OF AROMATICS IN AN AROMATICS COMPLEX

CROSS-REFERENCE TO RELATED APPLICATION

This application claims priority from Provisional Application No. 62/436,884 filed Dec. 20, 2016, the contents of which cited application are hereby incorporated by reference in its entirety.

FIELD

This present disclosure relates to processes and apparatuses for methylation of aromatics in an aromatics complex for producing a xylene isomer product. More specifically, the present disclosure relates to a process for producing para-xylene by the selective methylation of toluene and/or benzene in an aromatics complex.

BACKGROUND

The xylene isomers are produced in large volumes from petroleum as feedstocks for a variety of important industrial chemicals. The most important of the xylene isomers is para-xylene, the principal feedstock for polyester, which continues to enjoy a high growth rate from large base demand. Ortho-xylene is used to produce phthalic anhydride, which supplies high-volume but relatively mature markets. Meta-xylene is used in lesser but growing volumes for such products as plasticizers, azo dyes and wood preservers. Ethylbenzene generally is present in xylene mixtures and is occasionally recovered for styrene production, but is usually considered a less-desirable component of $C_8$ aromatics.

Among the aromatic hydrocarbons, the overall importance of xylenes rivals that of benzene as a feedstock for industrial chemicals. Xylenes and benzene are produced from petroleum by reforming naphtha but not in sufficient volume to meet demand, thus conversion of other hydrocarbons is necessary to increase the yield of xylenes and benzene. Often toluene is de-alkylated to produce benzene or selectively disproportionated to yield benzene and $C_8$ aromatics from which the individual xylene isomers are recovered.

An aromatics complex flow scheme has been disclosed by Meyers in the HANDBOOK OF PETROLEUM REFINING PROCESSES, 2d. Edition in 1997 by McGraw-Hill, and is incorporated herein by reference.

Traditional aromatics complexes send toluene to a transalkylation zone to generate desirable xylene isomers via transalkylation of the toluene with $A_{9+}$ components. $A_{9+}$ components are present in both the reformate bottoms and the transalkylation effluent.

Methylation of toluene or benzene with oxygenates such as methanol has been proposed as a pathway to make xylene and to increase methyl to phenyl ratio in the aromatic complex to maximize xylene production. Toluene methylation operating in vapor phase has a poor feed, especially oxygenate, utilization, low aromatics conversion per pass and poor catalyst stability in a time span of days and weeks, thus requiring frequent regeneration. Typically, toluene methylation is operating with selective para-xylene production objective, which requires operating under severe process conditions, namely high temperature when methanol decomposition to $CO_x$ and $H_2$ is significant, with a significant amount of diluents such as $H_2O$, $H_2$ and thus recycles using a catalyst relatively difficult to prepare reproducibly. MFI zeolite has been the catalyst used predominantly in this process.

Accordingly, it is desirable to provide improved methods and apparatuses for methylation of aromatic compounds such as toluene and benzene in an aromatics complex. Further, it is desirable to provide a cost-effective method and apparatus for toluene and/or benzene methylation which operates under mild conditions, promotes high utilization of the feedstock and where higher than equilibrium pX/X can be achieved without using dilution. Also, it is desirable to reduce the overall Capital Expenditure (CAPEX) and Operational Expenditure (OPEX) of operating and/or incorporating such a methylation unit in an aromatics complex. Furthermore, other desirable features and characteristics of the present subject matter will become apparent from the subsequent detailed description of the subject matter and the appended claims, taken in conjunction with the accompanying drawings and this background of the subject matter.

SUMMARY

The present subject matter relates to processes and apparatuses for toluene and/or benzene methylation in an aromatics complex for producing a xylene isomer. More specifically, the present disclosure relates to processes and apparatuses for toluene methylation under mild reaction conditions, namely a combination of low temperatures and elevated pressures. Under such conditions the process can operate in a liquid, mixed vapor-liquid or vapor phase, respectively, effectively maintaining methylation reactivity, minimizing methanol to non-aromatics (NA) formation and para-xylene or ortho-xylene formation above thermodynamic equilibria within an aromatics complex.

In accordance with an exemplary embodiment, a process is provided for producing a xylene isomer comprising reacting oxygenates with an aromatic feedstock comprising toluene and/or benzene in a methylation zone operating under alkylation conditions comprising a maximum temperature of about 150° C. to about 400° and a pressure of about 140 kPa to 6000 kPa in the presence of a catalyst composition comprising a zeolite selected from a member of the group consisting of UZM-8, UZM-37, MCM-22, MCM-49, MCM-56 to provide a product stream comprising the xylene isomer.

In accordance with another exemplary embodiment, a process is provided for producing para-xylene comprising reacting a toluene stream and a methanol stream in a toluene methylation zone operating under toluene methylation conditions comprising a maximum temperature of about 150° C. to about 400° C. and a pressure of about 10 kPa to 10,000 kPa in the presence of a catalyst composition comprising a zeolite selected from the group consisting of UZM-37 and MCM-22 to produce a product stream comprising para-xylene.

In accordance with yet another exemplary embodiment, a process is provided for producing para-xylene comprising reacting a toluene stream and a methanol stream in a toluene methylation zone operating under toluene methylation conditions comprising a maximum temperature of about 200° C. to about 350° C., a pressure of about 140 kPa to 6,000 kPa, a weight hourly space velocity is from 0.5 to 4 hr-1 and a toluene to methanol molar ratio of from about 1:1 to 6:1, in the presence of a catalyst composition comprising a zeolite selected from the group consisting of UZM-37 and MCM-22 to produce to produce a product stream comprising paraxylene.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

Definitions

As used herein, the term "stream", "feed", "product", "part" or "portion" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

Hydrocarbon molecules may be abbreviated $C_1$, $C_2$, $C_3$, Cn where "n" represents the number of carbon atoms in the one or more hydrocarbon molecules or the abbreviation may be used as an adjective for, e.g., non-aromatics or compounds. Similarly, aromatic compounds may be abbreviated $A_6$, $A_7$, $A_8$, An where "n" represents the number of carbon atoms in the one or more aromatic molecules. Furthermore, a subscript "+" or "−" may be used with an abbreviated one or more hydrocarbons notation, e.g., $C_{3+}$ or $C_{3-}$, which is inclusive of the abbreviated one or more hydrocarbons. As an example, the abbreviation "$C_{3+}$" means one or more hydrocarbon molecules of three or more carbon atoms.

As used herein, the term "zone" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally 50%, and preferably 70%, by mole, of a compound or class of compounds in a stream.

Figure 1:
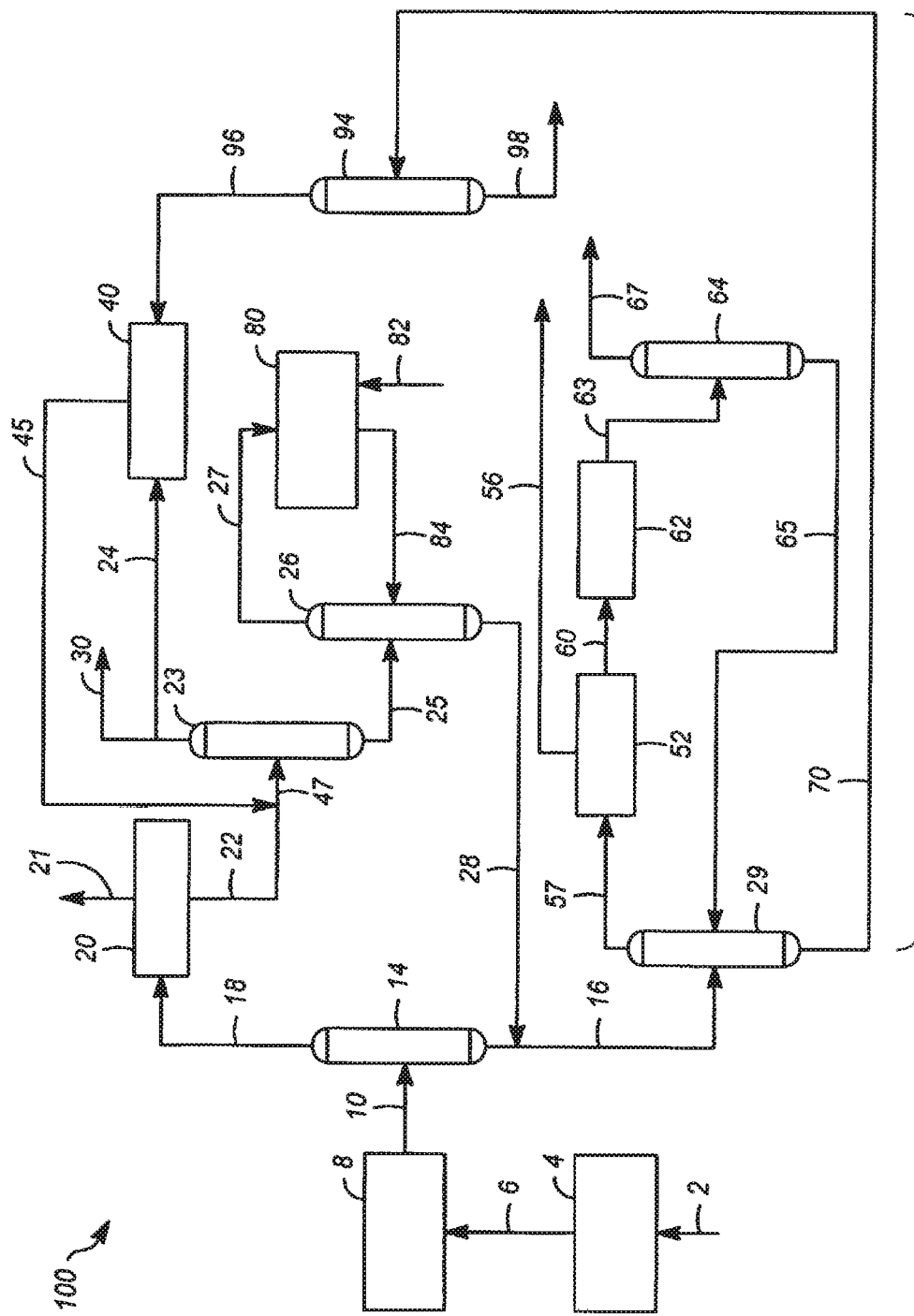
FIG. 1 illustrates an aromatics complex having an integrated toluene methylation zone according to an exemplary embodiment.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description. Moreover, the reaction conditions including selection of temperature, pressure, LHSV and catalyst in the various units in the aromatics complex described below are conventional which are known to one of ordinary skill in the art, unless wherever mentioned. The scope of the present disclosure should be determined with reference to the claims.

The feedstream to the present process generally comprises alkylaromatic hydrocarbons of the general formula $C_6H_{(6-n)}R_n$, where n is an integer from 0 to 5 and each R may be $CH_3$, $C_2H_5$, $C_3H_7$, or $C_4H_9$, in any combination. The aromatics-rich feed stream to the process of the present disclosure may be derived from a variety of sources, including without limitation conventional catalytic reforming, zeolitic reforming converting $C_6$-$C_7$ non-aromatics from light naphtha or aromatic extraction raffinates to benzene and toluene, steam pyrolysis of naphtha, distillates or other hydrocarbons to yield light olefins and aromatics-rich byproducts (including gasoline-range material often referred to as "pygas"), and catalytic or thermal cracking of distillates and heavy oils to yield products in the gasoline range. Products from pyrolysis or other cracking operations generally will be hydrotreated according to processes well known in the industry before being charged to the complex in order to remove sulfur, olefins and other compounds which would affect product quality and/or damage catalysts and downstream process. Light cycle oil from catalytic cracking also may be beneficially hydrotreated and/or hydrocracked according to known technology to yield products in the gasoline range; the hydrotreating preferably also applies to catalytic reforming to yield the aromatics-rich feed stream.

Various embodiments are directed to apparatuses and processes for producing a xylene isomer product in an aromatic complex having an integrated alkylation zone, wherein the process comprises reacting oxygenates with an aromatic feedstock in a methylation zone under alkylation condition in the presence of a catalyst composition in an alkylation catalyst bed to provide a product stream comprising the xylene isomer. In an aspect, the aromatic feedstock may include toluene. In another aspect, the aromatic feedstock may include benzene. In an embodiment, the aromatic feedstock may include both benzene and toluene. In one embodiment, benzene and toluene methylation occur in the same zone. In another embodiment, both benzene and toluene methylation zones may be present. In one aspect, benzene and toluene methylation may occur in separate and parallel zones. In an aspect, toluene methylation zone may be followed benzene methylation zone, where toluene generated in benzene methylation zone may be combined with fresh toluene before entering the toluene methylation zone. The alkylation condition may include a maximum temperature of from about of about 150° C. to about 400° C., preferably from about 200° C. to about 350° C. and more preferably from about 260° C. to about 320° C. In accordance with various embodiments, the maximum temperature may refer to the maximum temperature of the alkylation catalyst bed and may be interchangeably referred to as the maximum bed temperature. Further, the alkylation condition may include a pressure of from about 10 kPa to 10,000 kPa, preferably from about 140 kPa to 6000 kPa and more preferably from about 300 kPa to about 3000 kPa. The alkylation conditions may further include a weight hourly space velocity (WHSV) of from 0.1 to 10 hr$^{-1}$, preferably from about 0.5 to 4 hr$^{-1}$ and more preferably from about 1 to 2 hr$^{-1}$. Also, the alkylation conditions may include an aromatic feedstock to oxygenate molar ratio of from about 0.5:1 to 10:1, preferably from about 1:1 to 6:1 and more preferably from about 1.5:1 to 4:1. In an embodiment, the alkylation conditions may comprises a maximum temperature of less than about 500° C., of pressure of about 100 kPa to 6,000 kPa, and a toluene to methanol molar ratio of from about 1:2 to 6:1. The oxygenates may be selected from the group consisting of a methanol, a dimethylether and a dimethylcarbonate, a dimethylsulfate, and halogenated methanes. The catalyst may include a zeolite selected from a member of the group consisting of UZM-8, UZM-37, MCM-22, MCM-49, MCM-56. In some embodiments, other zeolites having MWW topology may be selected. In an aspect, the catalyst may include a MCM-22 zeolite and the product stream may comprise para-xylenes. In another aspect, the catalyst may include a UZM-8 zeolite and the product stream may comprise ortho-xylenes. In yet another aspect, the catalyst may include UZM-37 zeolite and the product stream may comprise para-xylenes. A refractory binder or matrix may be utilized to facilitate fabrication of the catalyst, providing strength and reduce fabrication costs. Suitable binders include inorganic oxides such as one or more of alumina, silica, magnesia, zirconia, chromia, titania, boria, thoria, phosphate, zinc oxide and the mixture of thereof. In accordance with an exemplary embodiment, alumina may be used a binder. In various embodiments, the alkylation is performed in one of a vapor phase, a liquid phase and a mixed vapor-liquid phase. In one embodiment, alkylation is performed in the mixed vapor-liquid phase. Applicants have found out that by operating low temperature and elevated regions covering liquid, a mixed vapor-liquid phase or vapor conditions good aromatic conversion and very high feed utilization of both aromatics and oxygenates is achieved. Further selectivity of the desired xylene isomer is also attained at a level above thermodynamic equilibria.

FIG. 1 is a simplified flow diagram of an exemplary aromatics-processing complex of the known art directed to the production of at least one xylene isomer. FIG. 1 is a simplified flow diagram of an exemplary aromatics-processing complex of the known art integrated with a toluene methylation unit directed to the production of at least one xylene isomer. The complex may process an aromatics-rich feed which has been derived, for example, from catalytic reforming in a reforming zone. The reforming zone generally includes a reforming unit that receives a feed. The reforming unit will typically comprise a reforming catalyst. Usually such a stream will also be treated to remove olefinic compounds and light ends, e.g., butanes and lighter hydrocarbons and preferably pentanes; such removal, however, is not essential to the practice of the broad aspects of this disclosure and is not shown. The aromatics-containing feed stream contains benzene, toluene and $C_8$ aromatics and typically contains higher aromatics and aliphatic hydrocarbons including naphthenes. The complex may also process additional benzene and toluene derived from converting $C_6$-$C_7$ non-aromatics from light naphtha and/or raffinates from the aromatic extraction units using zeolitic reforming processes to further increase aromatic production throughput.

According to an exemplary embodiment as shown in the FIG. 1, the process and apparatus 100 includes a hydrotreating zone 4, a naphtha splitter 14, a reforming zone 8, a reformate splitter 14, an aromatics extraction unit 20, a benzene column 23, a toluene column 26, a transalkylation zone 40, a toluene methylation unit 80, a xylene fractionation column 29, a heavy aromatics column 94, a para-xylene extraction unit, 52, a xylene isomerization unit 62, and an deheptanizer column 64.

In accordance with an exemplary embodiment as shown in FIG. 1, a hydrocarbon feedstream in line 2 may be passed to the hydrotreating zone 4. In accordance with the instant embodiment as discussed, the hydrocarbon feedstream in line 2 is a naphtha stream and hence interchangeably referred to as naphtha stream in line 2. The naphtha stream in line 2 may be provided to the hydrotreating zone 4 to produce a hydrotreated naphtha stream in line 6. As used herein, the term "naphtha" means the hydrocarbon material boiling in the range between about 10° C. and about 200° C. atmospheric equivalent boiling point (AEBP) as determined by any standard gas chromatographic simulated distillation method such as ASTM D2887, all of which are used by the petroleum industry. The hydrocarbon material may be more contaminated and contain a greater amount of aromatic compounds than is typically found in refinery products. The typical petroleum derived naphtha contains a wide variety of different hydrocarbon types including normal paraffins, branched paraffins, olefins, naphthenes, benzene, and alkyl aromatics. Although the present embodiment is exemplified by a naphtha feedstream, the process is not limited to a naphtha feedstream, and can include any feedstream with a composition that overlaps with a naphtha feedstream.

Referring to FIG. 1, the hydrotreating zone 4 may include one or more hydrotreating reactors for removing sulfur and nitrogen from the naphtha stream in line 2. A number of reactions take place in the hydrotreating zone 4 including hydrogenation of olefins and hydrodesulfurization of mercaptans and other organic sulfur compounds; both of which (olefins, and sulfur compounds) are present in the naphtha fractions. Examples of sulfur compounds that may be present include dimethyl sulfide, thiophenes, benzothiophenes, and the like. Further, reactions in the hydrotreating zone 4 include removal of heteroatoms, such as nitrogen and metals. Conventional hydrotreating reaction conditions are employed in the hydrotreating zone 4 which are known to one of ordinary skill in the art.

The hydrotreated naphtha stream in line 6 withdrawn from the hydrotreating zone 4 may be passed to the catalytic reforming unit in the reforming zone 8 to provide a reformate stream in line 10. In an aspect, the hydrotreated naphtha stream in line 6 may be passed to the catalytic reforming unit 8 to provide the reformate stream in line 10. The reforming conditions includes a temperature of from about 300° C. to about 500° C., and a pressure from about 0 kPa(g) to about 3500 kPa(g). Reforming catalysts generally comprise metals and halides dispersed on a support. This catalyst is conventionally a dual-function catalyst that includes a metal hydrogenation-dehydrogenation, a modifier on a refractory support. The support can include a porous material, such as an inorganic oxide or a molecular sieve, and a binder with a weight ratio from 1:99 to 99:1. In accordance with various embodiments, the reforming catalyst comprises a noble metal comprising one or more of platinum, palladium, rhodium, ruthenium, osmium, and iridium, and a modifier such as rhenium, tin and germanium. The reforming catalyst may be supported on refractory inorganic oxide support comprising one or more of alumina, a chlorided alumina a magnesia, a titania, a zirconia, a chromia, a zinc oxide, a thoria, a boria, a silica-alumina, a silica-magnesia, a chromia-alumina, an alumina-boria, a silica-zirconia and a zeolite.

The reformate feed stream in line 10 may be passed to reformate splitter 14 and distilled to separate a stream comprising $C_8$ and heavier aromatics, withdrawn as a bottoms stream via a bottoms outlet in line 16, from toluene and lighter hydrocarbons recovered as overhead stream in line 18. The toluene and lighter hydrocarbons are sent to extractive distillation process unit 20 which separates a aliphatic raffinate stream in line 21 from a benzene-toluene aromatics stream in line 22. The aliphatic raffinate stream made up of mainly $C_6$-$C_7$ non-aromatics can be converted to benzene and toluene efficiently using zeolitic reforming process as additional feed for benzene/toluene methylation, further increasing specific xylene isomer production. The aromatics stream in line 22 is separated, along with stripped transalkylation product in line 45 which enters the benzene column 23 into a benzene stream in line 24 and a toluene-and-heavier aromatics stream in line 25 which is sent to the toluene column 26. In accordance with an exemplary embodiment as shown in FIG. 1, the benzene stream in line 30 may be a product stream. The benzene stream in line 24 is passed from the benzene column 23 to the transalkylation unit 40. In one embodiment, the transalkylation conditions may include a temperature of about 320° C. to about 440° C. The transalkylation zone may contain a first catalyst. In one embodiment, the first catalyst comprises at least one zeolitic component suitable for transalkylation, at least one zeolitic component suitable for dealkylation and at least one metal component suitable for hydrogenation. A toluene stream is recovered overhead from the toluene column 26 in line 27 and may be sent partially or totally to the toluene methylation unit 80 along with a methanol stream in line 82 as shown and discussed hereinafter.

The methanol stream in line 82 and the toluene stream in line 27 is passed to the toluene methylation unit 80. In the toluene methylation unit 80, the toluene stream may react with the methanol stream under toluene methylation conditions in the presence of a catalyst in an alkylation catalyst bed. Although the instant embodiment has been discussed with respect to methanol, however, other oxygenates known in the art may be used in the process and are within the scope of the present disclosure. In accordance with an exemplary embodiment, the methanol stream is combined with toluene and fed into the toluene methylation unit 80 including a single reactor containing multiple catalyst beds having an arrangement between catalyst beds to remove heat of methylation. In another embodiment, the toluene methylation unit 80 may be a multiple reactor configuration operating in sequence with all toluene feed being passed through the first reactor and oxygenate feed is split and injected in parallel to separate reactors. In this specific embodiment, the interstage cooling can be implemented to control removal of the heat of reaction via heat exchanging with an incoming cool stream in order to attain an optimal operating temperatures. The toluene methylation may take place in one of vapor, a liquid phase and or a mixed vapor-liquid phase. A hydrocarbon stream in line 84 comprising para-xylenes may be withdrawn from the toluene methylation unit 80. The catalyst may include a zeolite selected from a member of the group consisting of UZM-8, UZM-37, MCM-22, MCM-49, MCM-56. In accordance with an exemplary embodiment, the catalyst may include a MCM-22 zeolite. In accordance with another exemplary embodiment, the catalyst may include a UZM-37 zeolite. A refractory binder or matrix may be utilized to facilitate fabrication of the catalyst, providing strength and reduce fabrication costs. Suitable binders include inorganic oxides such as one or more of alumina, silica, magnesia, zirconia, chromia, titania, boria, thoria, phosphate, zinc oxide and a mixture of thereof. In accordance with an exemplary embodiment, alumina may be used as a binder with UZM-37 or MCM-22 zeolite. The toluene methylation conditions may include a maximum temperature of from about of about 150° C. to about 400° C., preferably from about 200° C. to about 350° C. and more preferably from about 260° C. to about 320° C. In accordance with various embodiments, the maximum temperature may refer to the maximum temperature of the alkylation catalyst bed and may be interchangeably referred to as the maximum bed temperature. Further, the toluene methylation conditions may include a pressure of from about 10 kPa to 10,000 kPa, preferably from about 140 kPa to 6000 kPa and more preferably from about 300 kPa to about 3000 kPa. The toluene methylation conditions may include a weight hourly space velocity of from 0.1 to 10 $hr^{-1}$, preferably from about 0.5 to 4 $hr^{-1}$ and more preferably from about 1 to 2 $hr^{-1}$. Also, the alkylation conditions may comprise an aromatic feedstock to oxygenate molar ratio of from about 0.5:1 to 10:1, preferably from about 1:1 to 6:1 and more preferably from about 1.5:1 to 4:1. The hydrocarbon stream in line 84 is passed back to the toluene column 26. In one embodiment, the toluene methylation product stream has a paraxylene to total xylene ratio of at least about 0.2, or preferably at least about 0.5, or more preferably about 0.8 to 0.95.

The toluene column 26 produces a product stream in line 28 which may include para-xylene, meta-xylene, ortho-xylene and ethylbenzene. The product stream may further comprise unconverted methanol including dehydrated form of methanol. In accordance with an exemplary embodiment, methanol in the product stream may be less than about 50%, preferably less than about 20% and most preferably less than about 5% of methanol in the feed. In an embodiment, unconverted methanol may be recovered and recycled back to toluene methylation unit 80. The product stream stripped off oxygenates in line 28 passes via line 16 to para-xylene separation process 50. The separation process operates, preferably via adsorption employing an adsorbent and desorbent, to extract para-xylene in the para-xylene extraction unit 52, which separates para-xylene. The para-xylene may be purified in finishing column, yielding a para-xylene product via line 56. The raffinate, comprising a non-equilibrium mixture of xylene isomers and ethylbenzene, is sent via line 60 to xylene isomerization unit 62. The raffinate is isomerized in xylene isomerization unit 62, which contains an isomerization catalyst to provide a product approaching equilibrium concentrations of C8-aromatic isomers. In one embodiment, the isomerization conditions include a temperature of about 240° C. to about 440° C. Further, the xylene isomerization unit may include a catalyst comprising at least one zeolitic component suitable for xylene isomerization, at least one zeolitic component suitable for ethylbenzene conversion, and at least one metal component suitable for hydrogenation. In one embodiment, the isomerization process is carried out in the vapor phase. In yet another embodiment, the isomerization process is carried out in the liquid phase. In one embodiment, the isomerization process converts ethylbenzene by dealkylation to produce benzene. In another embodiment, the isomerization process converts ethylbenzene by isomerization to produce xylenes.

An isomerization product is withdrawn in line 63 and passed to the deheptanizer column 64, which removes $C_7$ and lighter hydrocarbons with bottoms passing via line 65 to xylene column 30 to separate $C_9$ and heavier materials from the isomerized $C_8$-aromatics. Overhead liquid from deheptanizer column 64 is sent to a stripper, which removes light materials overhead in line 67 from $C_6$ and $C_7$ materials which are sent to the extractive distillation unit for recovery of benzene and toluene values.

The xylene column bottoms stream in line 70 may be passed to the heavy aromatics column 94 to separate heavy aromatics comprising $C_{11+}$ alkylaromatic hydrocarbons from $C_9$ and $C_{10}$ alkylaromatics recovered as the heavy aromatics column overhead stream in line 96. The $C_{11+}$ alkylaromatic hydrocarbons may be withdrawn from the heavy aromatics column 94 as a bottoms stream in line 98. The heavy aromatics column overhead stream in line 96 rich in $C_9$ and $C_{10}$ alkylaromatics may be blended with the benzene-enriched stream in line 24 to provide the transalkylation feed stream in line 24 which may be subsequently provided to the transalkylation zone 40 for production of additional toluene as previously described.

There are many possible variations of this scheme within the known art, as the skilled routineer will recognize. For example, the entire $C_6$-$C_8$ reformate or only the benzene-containing portion may be subjected to extraction. Para-xylene may be recovered from a $C_8$-aromatic mixture by crystallization rather than adsorption. The separation zone may also contain a simulated moving bed adsorption unit. In one example, the simulated moving bed adsorption unit uses a desorbent with a lower boiling point than xylenes, such as toluene or benzene. In yet another embodiment, the simulated moving bed adsorption unit uses a desorbent with a higher boiling point than xylenes, such as paradiethylbenzene, paradiisopropylbenzene, tetralin, or paraethyltoluene. Meta-xylene as well as para-xylene may be recovered from a $C_8$-aromatic mixture by adsorption, and ortho-xylene may be recovered by fractionation. Specifically xylenes are passed onto to simulated moving bed unit (such as UOP's Sorbex™ unit) unit using para-xylene adsorbent and desorbent and raffinate is isomerized and recycled back to the simulated moving bed unit for para-xylene production. Alternatively, xylenes are passed onto the simulated moving bed unit using meta-xylene adsorbent and desorbent and raffinate is fractionated to produce para-xylene and ortho-xylene with ortho-xylene being optionally isomerized and recycled to the simulated moving bed unit. The latter scheme takes the advantages of low meta-xylene contents of the reaction effluents coming off toluene methylation of the present disclosure, and can be effectively utilized for one or more of meta-xylene, para-xylene and ortho-xylene production. Alternatively, the $C_9$– and heavier stream or the heavy-aromatics stream is processed using solvent extraction or solvent distillation with a polar solvent or stripping with steam or other media to separate highly condensed aromatics as a residual stream from $C_9$+ recycle to transalkylation. In some cases, the entire heavy-aromatic stream may be processed directly in the transalkylation unit. Further, a benzene methylation unit may be integrated in the aromatics complex, in alternative, or in addition to the toluene methylation unit. The present disclosure is useful in these and other variants of an aromatics-processing scheme, aspects of which are described in U.S. Pat. No. 6,740,788 which is incorporated herein by reference.

EXAMPLES

The following examples are intended to further illustrate the subject embodiments. These illustrations of different embodiments are not meant to limit the claims to the particular details of these examples. Table 1 enlists results corresponding to different zeolites as mentioned in the table used in the methylation process in an aromatic complex, in accordance with the present disclosure.

TABLE 1

| | Catalyst | | | | | | | | |
|---|---|---|---|---|---|---|---|---|---|
| | A | B | | C | | | D | | |
| Zeolite | UZM-54 (27) | UZM-8 | | UZM-8 | | | MCM-22 (26) | | |
| Binder | SiO$_2$ | SiO$_2$ | | Al$_2$O$_3$ | | | Al$_2$O$_3$ | | |
| Run # | 1 | 2 | | 3 | | 4 | | 5 | |
| Temp., ° C. (max bed) | 400 | 400 | | 400 | | 400 | | 250 | |
| WHSV, hr–1 | 6.4 | 6.4 | | 6.4 | | 6.4 | | 0.8 | 0.4 |
| P, psig | 45 | 45 | | 45 | | 45 | | 375 | 375 |
| Cofeed | MeOH | MeOH | | MeOH | | MeOH | | MeOH | MeOH |
| HOS | ~100 | 3 | 24 | 3 | 24 | 2-4.5 | 23 | 49 | 92 |
| Toluene/MeOH molar | 2:01 | 2:01 | 2:01 | 2:01 | 2:01 | 2:01 | 2:01 | 2:01 | 2:01 |
| Toluene conv., % | 31.5 | 41.68 | 38.54 | 38.14 | 39.09 | 47.8 | 46.92 | 20.49 | 31.97 |
| Yield, wt % (C-basis) | | | | | | | | | |
| C1-C5 (including unconverted MeOH/DME) | 0.787 | 0.213 | 0.16 | 0.48 | 0.499 | 0.183 | 0.185 | 0.935 | 0.232 |
| Bz | 0.55 | 4.13 | 0.28 | 1.29 | 0.07 | 4.24 | 3.8 | 0.01 | 0.02 |
| Tol | 63.94 | 54.58 | 57.2 | 57.6 | 56.44 | 48.6 | 49.39 | 76.17 | 64.23 |
| A8 | 24.27 | 29.39 | 31.44 | 29.42 | 31.26 | 35.13 | 34.82 | 17.48 | 25.96 |
| A9 (excl.indane) | 6.76 | 9.26 | 9.39 | 8.72 | 9.4 | 10.87 | 10.43 | 2.51 | 5.43 |
| A10 (excl. m-ndanes) | 2.4 | 1.6 | 0.8 | 1.85 | 0.93 | 0.42 | 0.33 | 0.34 | 0.86 |
| A11 + HexamethylBz + A12+ | 0.63 | 0.24 | 0.32 | 0.27 | 0.45 | 0.16 | 0.54 | 0.11 | 0.31 |
| ITN | 0.4 | 0.28 | 0.03 | 0.17 | 0.01 | 0.13 | 0.09 | 0.002 | 0.007 |
| DPM's | 0.26 | 0.12 | 0.33 | 0.05 | 0.8 | 0.14 | 0.31 | 2.41 | 2.85 |
| pX/X | 24.1 | 24.1 | 23.5 | 24.1 | 33.9 | 24.1 | 24.3 | 56.9 | 57.5 |
| Av. alkyl-#C (A8-A10) | 2.3 | 2.28 | 2.24 | 2.28 | 2.24 | 2.23 | 2.22 | 2.14 | 2.2 |

TABLE 1-continued

| | Catalyst | | | | | | | | |
|---|---|---|---|---|---|---|---|---|---|
| | A | | B | | C | | | D | |
| Av. length of alkyl group (A8-A10) | 1.062 | 1.006 | 1.003 | 1.005 | 1.002 | 1.003 | 1.003 | 1.001 | 1.001 |
| | Molar ratios, rel to Tol | | | | | | | | |
| Bz | 0.01 | 0.089 | 0.006 | 0.027 | 0.001 | 0.103 | 0.091 | 0 | 0 |
| MEB | 2.987 | 0.368 | 0.103 | 0.27 | 0.05 | 0.216 | 0.21 | 0.01 | 0.016 |
| DMEB | 0.302 | 0.106 | 0.039 | 0.09 | 0.03 | 0.053 | 0.034 | 0.008 | 0.013 |
| DEB | 0.019 | 0 | 0.001 | 0 | 0 | 0 | 0.001 | 0.005 | 0.005 |

Table 1 demonstrates the benefits of having a toluene methylation zone integrated within an aromatics complex in accordance with the present disclosure. As shown in the Table 1, UZM-8 zeolite and MCM-22 zeolite have higher potential as compared to UZM-54 zeolite, showing lower propensity to make non-aromatics, alkyl substituents on aromatics of greater than 1.0 (methyl). Furthermore when operating with MCM-22 at lower temperature and elevated pressures (Catalyst D, Run 5), pX/X significantly higher than equilibrium of 24 was obtained.

Furthermore as shown in Table 2 below, under conditions of low temperatures and elevated pressures, UZM-37 and MCM-22 of 26 to 73 Si/Al molar ratios showed toluene conversions approaching stoichiometric conversion, lower selectivity to non-aromatics (NA), lower alkyl substituents of greater than 1.0 carbon number (methyl) and greater than equilibrium para-xylene/xylene of 24. Table 2 further shows that UZM-8 catalyst under comparable reaction conditions showed greater than equilibrium ortho-xylene/xylenes ratios.

TABLE 2

| | Catalyst | | | | | |
|---|---|---|---|---|---|---|
| | E | F | G | H | I | J |
| zeolite | MCM-22 (47) | MCM-22 (47) | UZM-8 (20) | MCM-22 (73) | UZM-37 | MCM-22 (26) |
| binder | $Al_2O_3$ | $Al_2O_3$ | $Al_2O_3$ | $SiO_2$ | $SiO_2$ | $SiO_2$ |
| catalyst size | 20 × 40 mesh | 1/16 inch | 1/16 inch | 10 × 40 mesh | 10 × 20 mesh | 10 × 20 mesh |
| Run# | 6 | 7 | 8 | 9 | 10 | 11 |
| WHSV, hr−1 | 1.38 | 1.38 | | 1.37 | | |
| Cofeed | MeOH | MeOH | | | | |
| HOS | 2.0 | 20.0 | 10.9 | 8.76 | 16.40 | 15.00 |
| Temp., ° C. (max) | 265.1 | 260.9 | 256.7 | 255.74 | 257.21 | 268.1 |
| Temp., ° C. (average bed) | 246.2 | 249.9 | 242.6 | 245.77 | 251.31 | 248.9 |
| P, psig | 396 | 392.3 | 391.2 | 386.83 | 393.95 | 396 |
| A7/Me | 4.0 | 3.7 | 4.2 | 4.10 | 4.18 | 4.34 |
| | Yield, wt % (C-basis) | | | | | |
| C1 | 0.045 | 0.1 | 0.0 | 0.07 | 0.04 | 0.03 |
| C2s | 0.000 | 0.0 | 0.0 | 0.00 | 0.00 | 0.00 |
| C3s | 0.007 | 0.0 | 0.0 | 0.01 | 0.01 | 0.01 |
| C4= | 0.003 | 0.0 | 0.0 | 0.01 | 0.00 | 0.00 |
| C4 | 0.004 | 0.0 | 0.0 | 0.01 | 0.00 | 0.00 |
| Oxygenates | 0.360 | 0.4 | 0.8 | 0.57 | 0.20 | 0.05 |
| C5+ non-arom | 0.005 | 0.0 | 0.0 | 0.01 | 0.01 | 0.01 |
| Bz | 0.02 | 0.0 | 0.0 | 0.00 | 0.01 | 0.05 |
| Tol | 77.36 | 76.0 | 81.8 | 79.28 | 77.26 | 77.60 |
| A8 | 18.40 | 19.2 | 14.0 | 16.23 | 18.84 | 18.05 |
| A9 (excl.indane) | 2.52 | 2.8 | 2.4 | 2.22 | 2.53 | 2.77 |
| A10 (excl. m-indanes) | 0.40 | 0.5 | 0.4 | 0.43 | 0.33 | 0.47 |
| A11 | 0.08 | 0.1 | 0.1 | 0.10 | 0.05 | 0.12 |
| HexamethylBz | 0.02 | 0.0 | 0.0 | 0.03 | 0.01 | 0.04 |
| A12+ | 0.00 | 0.0 | 0.0 | 0.01 | 0.01 | 0.00 |
| ITN's (from U744) | 0.001 | 0.0 | 0.0 | 0.00 | 0.00 | 0.00 |
| DPM's | 0.77 | 1.0 | 0.3 | 1.02 | 0.69 | 0.79 |
| toluene conv., % | 19.7 | 20.9 | 15.2 | 17.76 | 19.91 | 19.67 |
| MeOH conv., % | 90.1 | 90.0 | 76.5 | 84.00 | 94.28 | 98.54 |
| Me to Me (A8-A12) | 92.66 | 91.35 | 95.5 | 88.88 | 93.27 | 92.97 |
| Me to NA | 1.762 | 2.057 | 1.4 | 2.93 | 1.65 | 1.40 |
| non-Me alkyl (A8-A10) | 0.577 | 0.609 | 0.4 | 0.89 | 0.57 | 0.55 |
| Me to A10+ Me | 5.003 | 5.981 | 2.7 | 7.30 | 4.51 | 5.07 |
| pX/X | 51.0 | 53.1 | 27.0 | 50.74 | 53.26 | 47.50 |

TABLE 2-continued

|  | Catalyst | | | | | |
| --- | --- | --- | --- | --- | --- | --- |
|  | E | F | G | H | I | J |
| oX/X | 35.3 | 34.0 | 58.7 | 37.34 | 34.43 | 34.80 |
| EB | 0.023 | 0.0 | 0.0 | 0.02 | 0.02 | 0.020 |
| MEB | 0.024 | 0.0 | 0.0 | 0.03 | 0.02 | 0.028 |
| DMEB | 0.011 | 0.0 | 0.0 | 0.02 | 0.01 | 0.008 |
| DEB | 0.000 | 0.0 | 0.0 | 0.00 | 0.00 | 0.000 |

Table 3 shows that high conversions, high ring retention and high feed utilization can be achieved over a range of toluene to methanol ratios and over a wide range of pressures. Only when the pressure reaches greater than 1400 psig, toluene and methanol conversions are depressed.

thermore, UZM-37 and MCM-22 produce para-xylene selectively over meta- and ortho-xylene in excess of the levels projected by thermodynamic equilibrium, while UZM-8 produces orthfig.o-xylene selectively at a level projected by equilibrium. The lab plant tests shows that there

TABLE 3

| 65/35 H-MCM-22 (Si/Al2~47)/Al2O3, whole pills | | | | | | | |
| --- | --- | --- | --- | --- | --- | --- | --- |
|  | Run# | | | | | | |
|  |  |  | 12 |  |  | 13 | 14 |
| WHSV, hr−1 | 1.382 | 1.373 | 1.368 | 1.38 | 1.37 | 1.37 | 1.37 |
| Cofeed |  | MeOH |  | MeOH | MeOH | MeOH | MeOH |
| HOS | 11 | 29 | 37 | 69.1 | 52.0 | 81.1 | 53-68 |
| Temp., ° C. (max) | 267 | 272 | 272 | 274.3 | 272.8 | 271.4 | 275.1 |
| Temp., ° C. (average bed) | 256 | 259 | 259 | 263.8 | 262.0 | 262.7 | 258.8 |
| P, psig | 392 | 393 | 393 | 1429 | 1433 | 56 | 99 |
| A7/Me | 3.2 | 2.0 | 1.7 | 3.8 | 1.6 | 2.2 | 2.2 |
| Yield, wt % (C-basis) | | | | | | | |
| C1 | 0.050 | 0.087 | 0.110 | 0.059 | 0.073 | 0.032 | 0.028 |
| C2s | 0.000 | 0.000 | 0.000 | 0.000 | 0.004 | 0.003 | 0.000 |
| C3s | 0.008 | 0.009 | 0.011 | 0.006 | 0.010 | 0.007 | 0.004 |
| C4= | 0.003 | 0.006 | 0.006 | 0.005 | 0.009 | 0.000 | 0.001 |
| C4 | 0.004 | 0.005 | 0.009 | 0.011 | 0.007 | 0.003 | 0.001 |
| Oxygenates (water-free basis) | 0.391 | 0.566 | 1.124 | 1.699 | 7.233 | 0.081 | 0.053 |
| C5+ non-arom | 0.008 | 0.014 | 0.017 | 0.009 | 0.015 | 0.023 | 0.011 |
| Bz | 0.029 | 0.023 | 0.024 | 0.001 | 0.000 | 0.092 | 0.042 |
| Tol | 72.969 | 60.573 | 56.041 | 83.228 | 82.574 | 61.952 | 60.876 |
| A8 | 20.982 | 27.453 | 28.809 | 12.887 | 8.351 | 26.446 | 26.955 |
| A9 (excl.indane) | 3.641 | 7.357 | 8.846 | 0.959 | 0.503 | 8.629 | 9.830 |
| A10 (excl. m-indanes) | 0.715 | 1.861 | 2.388 | 0.107 | 0.074 | 1.542 | 1.416 |
| A11 | 0.189 | 0.561 | 0.745 | 0.029 | 0.022 | 0.524 | 0.307 |
| HexamethylBz | 0.081 | 0.241 | 0.270 | 0.009 | 0.007 | 0.167 | 0.062 |
| A12+ | 0.010 | 0.031 | 0.052 | 0.015 | 0.016 | 0.007 | 0.007 |
| ITN's | 0.000 | 0.001 | 0.003 | 0.000 | 0.001 | 0.004 | 0.003 |
| DPM's | 0.919 | 1.214 | 1.545 | 0.975 | 1.103 | 0.489 | 0.404 |
| toluene conv., % | 23.6 | 34.8 | 38.8 | 13.4 | 9.6 | 33.8 | 34.8 |
| MeOH conv., % | 91.3 | 91.9 | 86.6 | 55.6 | 16.7 | 98.7 | 99.2 |
| Me to Me (A8-A12) | 93.7 | 94.5 | 93.8 | 86.8 | 77.9 | 97.6 | 98.1 |
| Me to NA | 0.9 | 0.9 | 1.0 | 2.2 | 4.2 | 0.4 | 0.3 |
| non-Me alkyl (A8-A10) | 0.5 | 0.4 | 0.4 | 1.0 | 1.3 | 0.3 | 0.2 |
| Me to 2-R Me | 4.9 | 4.2 | 4.9 | 10.0 | 16.6 | 1.7 | 1.4 |
| pX/X | 50.622 | 53.953 | 55.384 | 63.6 | 65.6 | 44.7 | 48.8 |
| oX/X | 34.318 | 32.240 | 30.898 | 26.4 | 25.1 | 27.4 | 25.9 |
| EB | 0.023 | 0.020 | 0.019 | 0.025 | 0.023 | 0.0175 | 0.0169 |
| MEB | 0.032 | 0.029 | 0.031 | 0.016 | 0.013 | 0.0279 | 0.0201 |
| DMEB | 0.012 | 0.023 | 0.027 | 0.021 | 0.018 | 0.0110 | 0.0093 |
| DEB | 0.000 | 0.000 | 0.000 | 0.000 | 0.000 | 0.0000 | 0.0000 |

Figure 2:
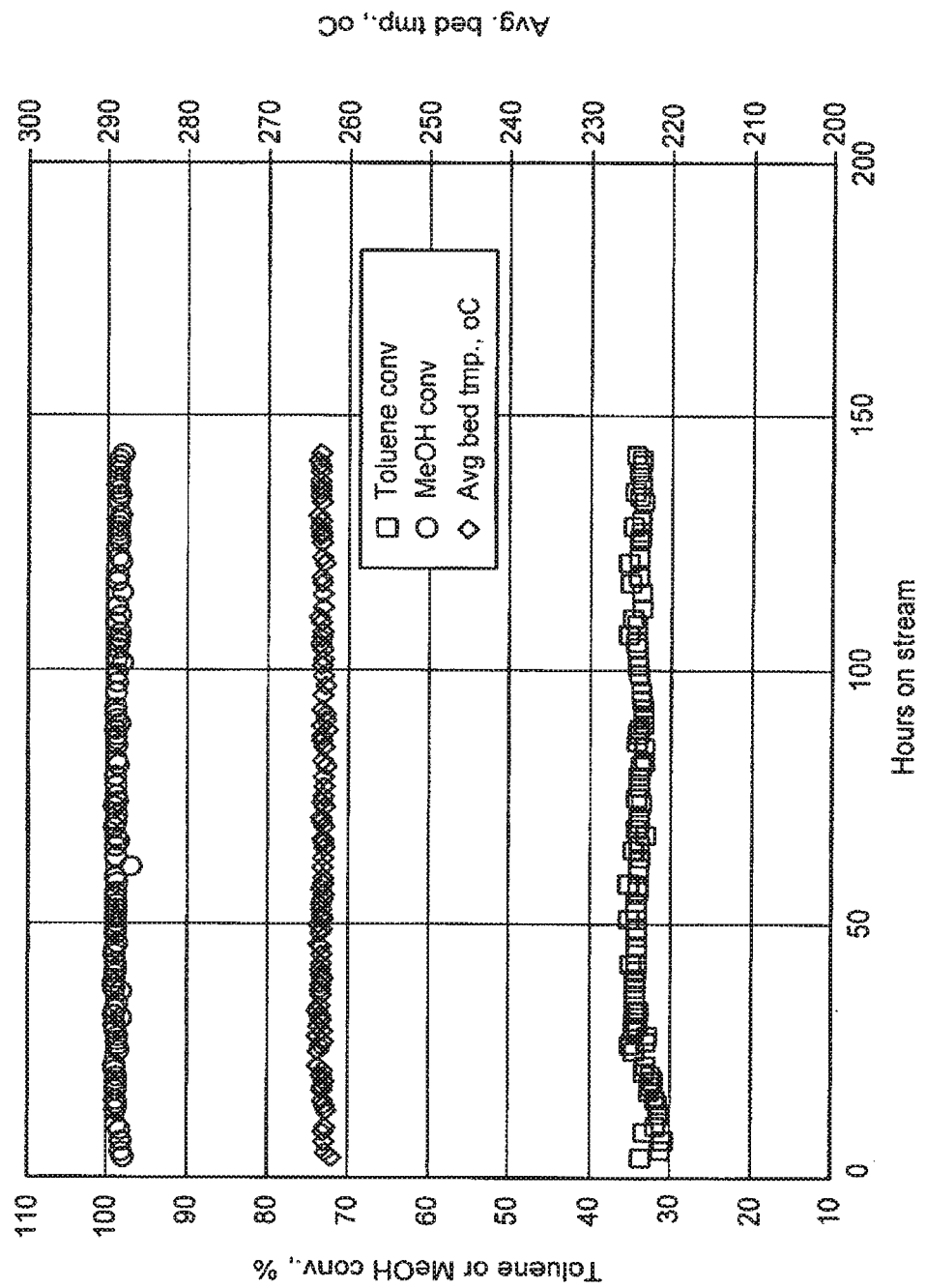
FIG. 2 illustrates lab plant test results.
Figure 3:
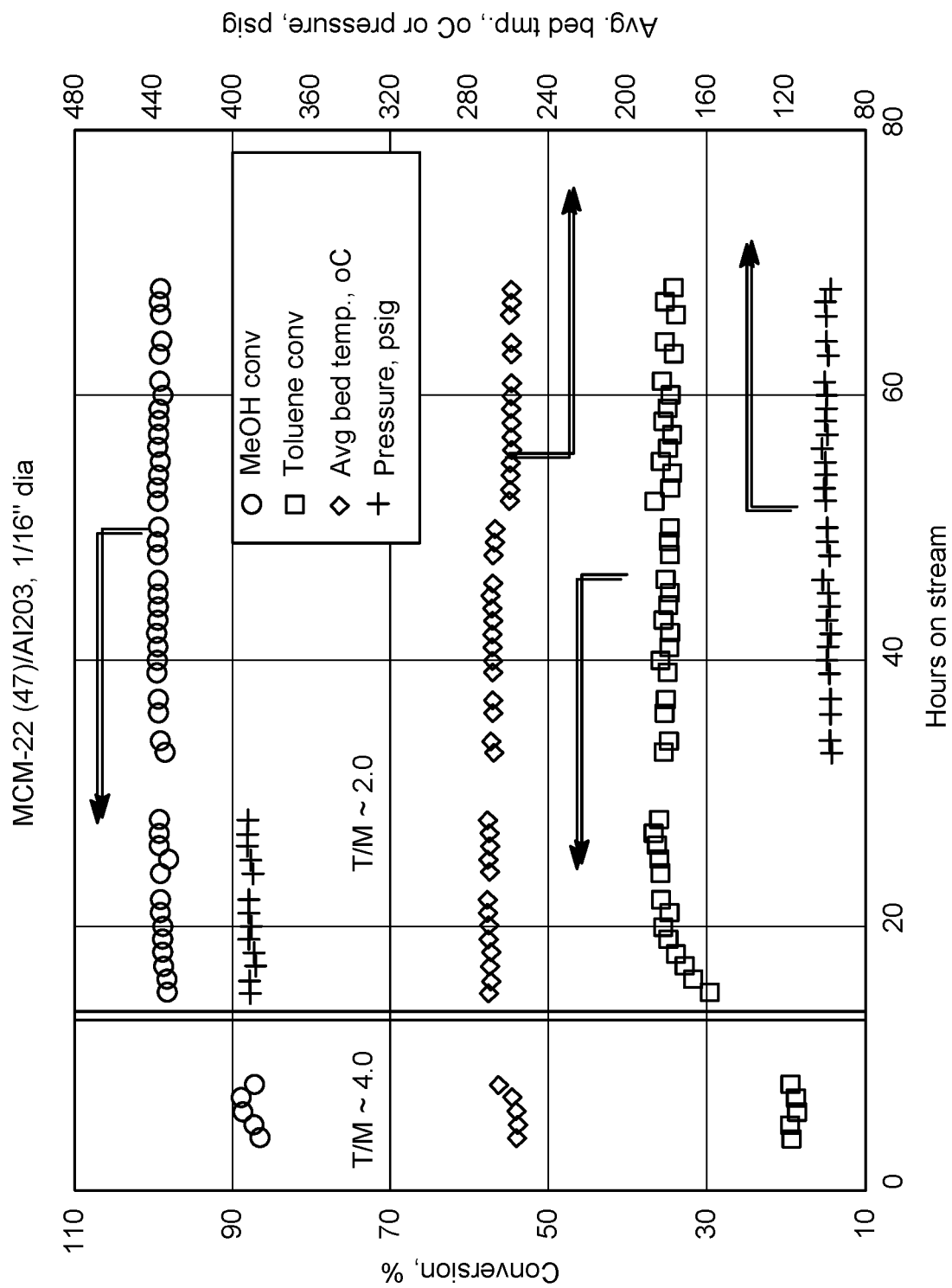
FIG. 3 illustrates more lab plant test results.

As shown in Tables 1, 2 and 3, UZM-8, UZM-37 and MCM-22, when operating at low temperatures over a range of elevated pressures gave high toluene and methanol conversion, low non-aromatics, low ethylated aromatics. Furthermore, was no sign of catalyst deactivation over a period of days or weeks as shown in FIGS. 2 and 3, using both UZM-8 and MCM-22 zeolites. Also, it is evident from MCM-22 of a wide range of Si/Al ratios at different catalyst sizes, using either a silica or a alumina binder does result in comparable performance with respect to overall conversion and selectivity.

Also, both UZM-8 and MCM-22 zeolites exhibit exceptional methylation selectivity. The selectivity to all ethylated aromatic products in A8-A10 range does exceeds 1%, and under appropriate conditions i.e. low temperatures and elevated pressures can be kept at or below 0.2%. Further, it is believed that as a result of high methylation selectivity the formation of indanes, tetralins and naphthalenes is also very low as the methyl groups are not long enough to form the second ring.

It should be noted that various changes and modifications to the presently preferred embodiments described herein will be apparent to those skilled in the art. Such changes and modifications may be made without departing from the spirit and scope of the present subject matter and without diminishing its attendant advantages.

SPECIFIC EMBODIMENTS

While the following is described in conjunction with specific embodiments, it will be understood that this description is intended to illustrate and not limit the scope of the preceding description and the appended claims.

A first embodiment of the invention is a process for producing a xylene isomer comprising reacting oxygenates with an aromatic feedstock comprising toluene and/or benzene in a methylation zone operating under alkylation conditions comprising a maximum temperature of about 150° C. to about 400° and a pressure of about 140 kPa to 6000 kPa in the presence of a catalyst composition comprising a zeolite selected from a member of the group consisting of UZM-8, UZM-37, MCM-22, MCM-49, MCM-56 to provide a product stream comprising the xylene isomer. An embodiment of the invention is one, any or all of prior embodiments in this paragraph up through the first embodiment in this paragraph, wherein the oxygenate is selected from the group consisting of a methanol, a dimethylether and a dimethylcarbonate, a dimethylsulfate, and halogenated methanes. An embodiment of the invention is one, any or all of prior embodiments in this paragraph up through the first embodiment in this paragraph, wherein the catalyst comprises a MCM-22 zeolite and product stream comprises para-xylenes. An embodiment of the invention is one, any or all of prior embodiments in this paragraph up through the first embodiment in this paragraph, wherein the catalyst comprises a UZM-37 zeolite and product stream comprises para-xylenes. An embodiment of the invention is one, any or all of prior embodiments in this paragraph up through the first embodiment in this paragraph, wherein the catalyst comprises UZM-8 zeolite and the product stream comprises ortho-xylenes. An embodiment of the invention is one, any or all of prior embodiments in this paragraph up through the first embodiment in this paragraph, wherein the alkylation is performed in one of a vapor phase, a liquid phase and or a mixed vapor-liquid phase. An embodiment of the invention is one, any or all of prior embodiments in this paragraph up through the first embodiment in this paragraph, wherein the alkylation conditions comprise a maximum temperature of about 200° C. to about 350° C. An embodiment of the invention is one, any or all of prior embodiments in this paragraph up through the first embodiment in this paragraph, wherein the alkylation conditions comprise a pressure of about 300 kPa to about 3000 kPa. An embodiment of the invention is one, any or all of prior embodiments in this paragraph up through the first embodiment in this paragraph, wherein the alkylation conditions comprise a weight hourly space velocity of from about 0.5 to 4.

A second embodiment of the invention is a process for producing paraxylene comprising reacting a toluene stream and a methanol stream in a toluene methylation zone operating under toluene methylation conditions comprising a temperature of about 150° C. to about 400° C. and a pressure of pressure of about 10 kPa to 10,000 kPa in the presence of a catalyst composition comprising a zeolite MCM-22 to produce a product stream comprising para-xylene. An embodiment of the invention is one, any or all of prior embodiments in this paragraph up through the second embodiment in this paragraph, wherein the toluene methylation conditions comprise a temperature of about 200° C. to about 350° C. An embodiment of the invention is one, any or all of prior embodiments in this paragraph up through the second embodiment in this paragraph, wherein the toluene methylation conditions comprise a temperature of about 260° C. to about 320° C. An embodiment of the invention is one, any or all of prior embodiments in this paragraph up through the second embodiment in this paragraph, wherein the toluene methylation conditions comprise a pressure of about 140 kPa to about 6000 kPa. An embodiment of the invention is one, any or all of prior embodiments in this paragraph up through the second embodiment in this paragraph, wherein the toluene methylation conditions comprise a pressure of about 300 kPa to about 3000 kPa. An embodiment of the invention is one, any or all of prior embodiments in this paragraph up through the second embodiment in this paragraph, wherein the toluene methylation conditions comprise a weight hourly space velocity is from 0.1 to 10 hr-1. An embodiment of the invention is one, any or all of prior embodiments in this paragraph up through the second embodiment in this paragraph, wherein the toluene methylation conditions comprise a weight hourly space velocity is from 0.5 to 4 hr-1. An embodiment of the invention is one, any or all of prior embodiments in this paragraph up through the second embodiment in this paragraph, wherein the toluene methylation conditions comprise a weight hourly space velocity is from 1 to 2 hr-1. An embodiment of the invention is one, any or all of prior embodiments in this paragraph up through the second embodiment in this paragraph, wherein toluene methylation conditions comprise a toluene to methanol molar ratio of from about 0.51 to 101. An embodiment of the invention is one, any or all of prior embodiments in this paragraph up through the second embodiment in this paragraph, wherein toluene methylation conditions comprise a toluene to methanol molar ratio of from about 1:1 to 6:1. An embodiment of the invention is one, any or all of prior embodiments in this paragraph up through the second embodiment in this paragraph, wherein toluene methylation conditions comprise a toluene to methanol molar ratio of from about 1.5:1 to 4:1. An embodiment of the invention is one, any or all of prior embodiments in this paragraph up through the second embodiment in this paragraph, wherein the toluene methylation is performed in one of a vapor phase, a liquid phase and or a mixed vapor-liquid phase.

A third embodiment of the invention is a process for producing para-xylene comprising reacting a toluene stream and a methanol stream in a toluene methylation zone operating under toluene methylation conditions comprising a temperature of about 200° C. to about 350° C., a pressure of pressure of about 140 kPa to 6,000 kPa, a weight hourly space velocity is from 0.5 to 4 hr-1 and a toluene to methanol molar ratio of from about 1:1 to 6:1, in the presence of a catalyst composition comprising a zeolite MCM-22 to produce to produce a product stream comprising para-xylene.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for producing a xylene isomer consisting essentially of:
   introducing a feedstock consisting essentially of an aromatic feedstream and an oxygenate feedstream into a methylation zone, wherein the aromatic feedstream consists essentially of toluene and/or benzene, and wherein the oxygenate feedstream is selected from the group consisting of methanol, dimethylether, dimethylcarbonate, dimethylsulfate, and halogenated methanes; and
   reacting the oxygenate feedstream with the aromatic feedstream in the methylation zone operating under alkylation conditions comprising a temperature of about 150° C. to about 275.1° C. and a pressure of about 10 kPa(g) to 386 kPa(g) in the presence of a catalyst composition comprising a zeolite selected from the group consisting of UZM-8, UZM-37, MCM-22, MCM-49, and MCM-56 to provide a product stream comprising the xylene isomer, wherein a ratio of para-xylene to xylenes in the product stream is greater than an equilibrium ratio of para-xylene to xylenes.

2. The process of claim 1, wherein the oxygenate feedstream is selected from the group consisting of methanol, dimethylether, dimethylcarbonate, and dimethylsulfate.

3. The process of claim 1, wherein the catalyst composition comprises a MCM-22 zeolite and the product stream comprises para-xylene.

4. The process of claim 1, wherein the catalyst composition comprises a UZM-37 zeolite and the product stream comprises para-xylene.

5. The process of claim 1, wherein the catalyst composition comprises UZM-8 zeolite and the product stream comprises ortho-xylene.

6. The process of claim 1, wherein reacting the oxygenate feedstream with the aromatic feedstream is performed in a vapor phase.

7. The process of claim 1, wherein the alkylation conditions comprise a pressure of about 10 kPa(g) to about 300 kPa(g).

8. The process of claim 1, wherein the alkylation conditions comprise a weight hourly space velocity of from about 0.5 to about 10 $hr^{-1}$.

9. The process of claim 1 wherein the temperature is about 150° C. to about 260° C.

10. The process of claim 1 wherein the temperature is about 150° C. to about 250° C.

11. The process of claim 1 wherein the temperature is about 150° C. to about 200° C.

12. A process for producing para-xylene consisting essentially of:
    introducing a feedstock consisting essentially of a toluene stream and a methanol stream into a toluene methylation zone, wherein the toluene stream consists essentially of toluene and the methanol stream consists essentially of methanol; and
    reacting the toluene stream and the methanol stream in the toluene methylation zone operating under toluene methylation conditions comprising a temperature of about 150° C. to about 275.1° C. and a pressure of about 10 kPa(g) to 386 kPa(g) in the presence of a catalyst composition comprising a zeolite MCM-22 to produce a product stream comprising para-xylene, wherein a ratio of para-xylene to xylenes in the product stream is greater than an equilibrium ratio of para-xylene to xylenes.

13. The process of claim 12, wherein the toluene methylation conditions comprise a pressure of about 140 kPa(g) to about 386 kPa(g).

14. The process of claim 12, wherein the toluene methylation conditions comprise a pressure of about 10 kPa(g), to about 300 kPa(g).

15. The process of claim 12, wherein the toluene methylation conditions comprise a weight hourly space velocity of from 0.1 to 10 $hr^{-1}$.

16. The process of claim 12, wherein the toluene methylation conditions comprise a weight hourly space velocity of from 0.5 to 4 $hr^{-1}$.

17. The process of claim 12, wherein the toluene methylation conditions comprise a toluene to methanol molar ratio of from about 0.5:1 to 10:1.

18. The process of claim 12, wherein the toluene methylation conditions comprise a toluene to methanol molar ratio of from about 1:1 to 6:1.

19. The process of claim 12, wherein reacting the methanol stream with the toluene stream is performed in a vapor phase.

20. A process for producing para-xylene consisting essentially of:
    introducing a feedstock consisting essentially of a toluene stream and a methanol stream into a toluene methylation zone, wherein the toluene system consists essentially of toluene and the methanol stream consists essentially of methanol; and
    reacting the toluene stream and the methanol stream in the toluene methylation zone operating under toluene methylation conditions comprising a temperature of about 150° C. to about 275.1° C., a pressure of about 140 kPa(g) to 386 kPa(g), a weight hourly space velocity of from 0.5 to 4 $hr^{-1}$ and a toluene to methanol molar ratio of from about 1:1 to 6:1, in the presence of a catalyst composition comprising a zeolite MCM-22 to produce a product stream comprising para-xylene, wherein a ratio of para-xylene to xylene in the product stream is greater than an equilibrium ratio of para-xylene to xylenes, and wherein the reacting is performed in a vapor phase.

* * * * *